United States Patent [19]

Ruka

[11] Patent Number: 4,631,238
[45] Date of Patent: Dec. 23, 1986

[54] COBALT DOPED LANTHANUM CHROMITE MATERIAL SUITABLE FOR HIGH TEMPERATURE USE

[75] Inventor: Roswell J. Ruka, Churchill, Pa.

[73] Assignee: Westinghouse Electric Corp., Pittsburgh, Pa.

[21] Appl. No.: 692,813

[22] Filed: Jan. 18, 1985

[51] Int. Cl.$^4$ .............................................. H01M 8/12
[52] U.S. Cl. ........................................ 429/30; 429/31; 429/191; 429/193; 252/519; 252/521; 501/152
[58] Field of Search ..................... 429/30, 31, 33, 32, 429/191, 193, 104; 252/519, 521; 501/152; 423/594, 595

[56] References Cited

U.S. PATENT DOCUMENTS

| | | | |
|---|---|---|---|
| 3,460,991 | 8/1969 | White, Jr. ............................... | 429/30 |
| 3,533,849 | 10/1970 | Mitoff ..................................... | 429/30 |
| 4,035,266 | 7/1977 | Alexandrov et al. .................. | 252/512 |
| 4,174,260 | 11/1979 | Schmidberger ................... | 429/31 X |
| 4,395,468 | 7/1983 | Isenberg ................................ | 429/31 |
| 4,490,444 | 12/1984 | Isenberg et al. ....................... | 429/31 |
| 4,547,437 | 10/1985 | Isenberg et al. ....................... | 429/30 |

Primary Examiner—Anthony Skapars
Attorney, Agent, or Firm—Daniel P. Cillo

[57] ABSTRACT

A high temperature, solid electrolyte electrochemical cell, subject to thermal cycling temperatures of between about 25° C. and about 1200° C., capable of electronic interconnection to at least one other electrochemical cell and capable of operating in an environment containing oxygen and a fuel, is made; where the cell has a first and second electrode with solid electrolyte between them, where an improved interconnect material is applied along a portion of a supporting electrode; where the interconnect is made of a chemically modified lanthanum chromite, containing cobalt as the important additive, which interconnect allows for adjustment of the thermal expansion of the interconnect material to more nearly match that of other cell components, such as zirconia electrolyte, and is stable in oxygen containing atmospheres such as air and in fuel environments.

12 Claims, 2 Drawing Figures

COBALT DOPED LANTHANUM CHROMITE MATERIAL SUITABLE FOR HIGH TEMPERATURE USE

GOVERNMENT CONTRACT

The Government of the United States of America has rights in this invention pursuant to Contract No. DE-AC-0280-ET-17089, awarded by the U.S. Department of Energy.

BACKGROUND OF THE INVENTION

High temperature fuel cell generators employing interconnected, tubular fuel cells, with solid electrolytes, are taught by A. O. Isenberg, in U.S. Pat. No. 4,395,468. Fuel electrode, air electrode, solid electrolyte and interconnection configurations for individual fuel cells, are taught by A. O. Isenberg, in U.S. Pat. No. 4,490,444. Usually, a porous support tube of calcia stabilized zirconia, approximately 1 millimeter to 2 millimeters thick, has an air electrode deposited on it. The air electrode is from about 50 microns to 1000 microns thick (0.05 millimeter to 1 millimeter) and may be made of doped and undoped oxides or mixtures of oxides, such as $LaMnO_3$, $CaMnO_3$, $LaNiO_3$, $LaCoO_3$, $LaCrO_3$, etc. Surrounding part of the outer periphery of the air electrode is a layer of gas-tight solid electrolyte, usually yttria stabilized zirconia, approximately 1 micron to 100 microns (0.001 millimeter to 0.1 millimeter) thick.

A selected radial segment of the air electrode not covered by electrolyte is covered by an interconnect material. The interconnect material is made of a lanthanum chromite film, of approximately 30 microns to 100 microns (0.03 millimeter to 0.1 millimeter) thickness. The synthesis of lanthanum chromite generally, is described by Alexandrov et al., in U.S. Pat. No. 4,035,266. The lanthanum chromite, for fuel cell interconnect application, is doped with one of calcium, strontium, or magnesium. Substantially surrounding the solid electrolyte is a second porous electrode which will be contacted with fuel during cell operation. This electrode is usually a nickel-zirconia or cobalt-zirconia cermet material. Deposited over the interconnect but not contacting the fuel electrode is a layer comprised of the same material as the fuel electrode.

The typical operating temperature of the solid oxide electrolyte fuel cell is from about 800° C. to about 1200° C. These fuel cells must be able to withstand occasional thermal cycling between about 25° C. and their maximum 1200° C. operating temperature. During these thermal cycles, all of the components must have a close match of thermal expansion characteristics in order to eliminate mechanical stresses, which can cause component layer cracking, with resultant leakage of oxygen and/or fuel and degradation of electrical characteristics of the cell. The components must also remain intact at the temperatures required during fuel cell fabrication, which may be as high as 1600° C. It has been found that the thermal expansion match of the solid electrolyte or mixed oxide electrode materials with the interconnect could be improved. Any change, however, must not reduce the electrical conductivity and ion transfer rates in the cell.

SUMMARY OF THE INVENTION

The above problem has been solved and the above needs met, most generally, by providing a novel, cobalt doped lanthanum chromite material, which has a good thermal expansion match with yttria stabilized zirconia solid electrolyte, and which has excellent high temperature stability, good electrical conductivity, and appropriate, very low ion transfer rates. This novel material can also be readily applied to a solid electrolyte or mixed oxide electrode.

This cobalt doped lanthanum chromite can be applied as an electronic interconnect, along a portion of a supporting solid electrode not covered by electrolyte in a high temperature electrochemical cell which is subject to thermal cycling between about 25° C. and about 1200° C. The cell is capable of connection to at least one other high temperature electrochemical cell, and the interconnect material is capable of operating in an environment containing oxygen or a fuel gas. The interconnect can act as an electronic connection to an electrode of a second electrochemical cell. The interconnect is nearly impermeable to both oxygen gas and oxygen ions and the composition can be adjusted to have an average coefficient of thermal expansion approximately the same as the solid electrolyte in the temperature range of between about 25° C. and about 1200° C.

A preferred material meeting all of these very restrictive properties is lanthanum chromite doped with both magnesium and cobalt, which has the chemical formula:

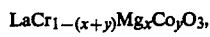

$$LaCr_{1-(x+y)}Mg_xCo_yO_3,$$

where $x =$ from about 0.005 to about 0.1, and $y =$ from about 0.005 to about 0.1. At $x = 0.03$ and $y = 0.05$, for example, the double doped lanthanum chromite has a good electrical conductivity, and a good thermal expansion match with yttria stabilized zirconia solid electrolyte, and also with the calcia stabilized zirconia support tube which comprises the most volume of the fuel cell, and which itself has a good thermal expansion match to the other components.

This conductive, interconnect material can be disposed on top of a supporting electrode in flat or tubular fuel cells at a thickness of from about 30 microns to about 100 microns and can be applied by any of a variety of techniques. In addition to use as an interconnect in electrochemical cells, this material could also find use as a heater element, or the like for high temperature use.

BRIEF DESCRIPTION OF THE DRAWINGS

For a better understanding of the invention, reference may be made to one embodiment exemplary of the invention, shown in the accompanying drawings, in which.

DESCRIPTION OF THE PREFERRED EMBODIMENTS

As shown in U.S. Pat. No. 4,395,468, herein incorporated by reference, a fuel cell arrangement or stack can comprise a plurality of elongated annular fuel cells. Each fuel cell is preferably tubular and is electrically connected at least in series to an adjacent cell. The electrical connection is made along a selected axial length of the cells, preferably the entire electrochemically active length. A typical cell generates an open circuit voltage of approximately one volt, and multiple cells can be connected in series in order to provide a desired system voltage.

Figure 1:
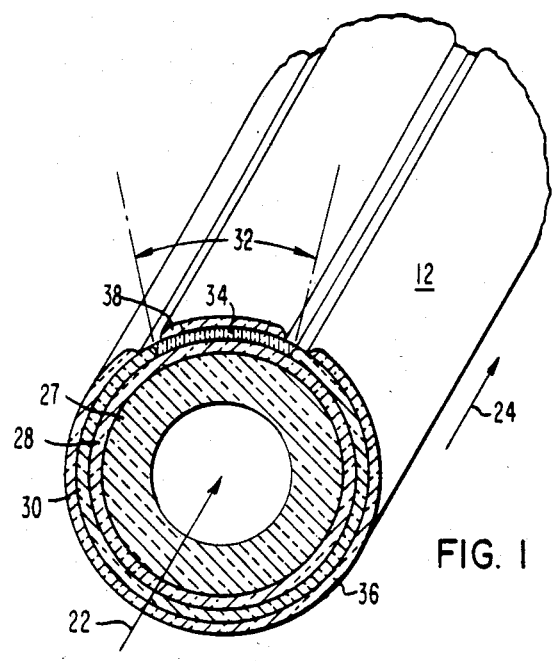
FIG. 1 is a schematic section view of a single tubular type fuel cell showing the interconnect of this invention on top of a supporting electrode.

FIG. 1 of the Drawings shows the preferred configuration for the fuel cells of this invention. The preferred configuration is based upon a system wherein a flowing gaseous fuel, such as hydrogen or carbon monoxide, is directed axially over the outside of the cell 12, as indicated by the arrow 24, and an oxidant, such as air, or $O_2$ indicated by the arrow 22, flows through the inside of the cell. It will be recognized that the location of the reactant fuel and oxidant can be interchanged such that air, or $O_2$ flows about the cells and fuel flows within the cells. This, requires the reversal of the cell electrodes. Where the cell is as shown, oxygen molecules pass through support and air electrode and are changed to oxygen ions which pass through the electrolyte to combine with fuel at the fuel electrode. It should be noted that the following description of the prepared tubular configuration should not be considered limiting. It should also be noted that the interconnect material of this invention could be applied to electrochemical cells other than fuel cells. The term "air electrode" as used throughout means that electrode which will be in contact with oxidant, and "fuel" electrode means that electrode that will be in contact with fuel.

In preferred form, each cell 12 includes a porous support tube 27 which provides structural integrity to the cell. In an exemplary cell 12, the support tube is comprised of calcia stabilized zirconia, forming a porous wall approximately one to two millimeters thick. Surrounding the outer periphery of the support tube 27 is a thin layer porous air electrode, or cathode 28. The exemplary system cathode 28 is a composite oxide structure approximately 50 microns to 1000 microns (0.05 millimeter to 1 millimeter) thick, which is deposited onto the support tube through well-known techniques. The air cathode is, for example, comprised of doped and undoped oxides or mixtures of oxides, such as $LaMnO_3$, $CaMnO_3$, $LaNiO_3$, $LaCoO_3$, $LaCrO_3$, doped indium oxide ($In_2O_3$), various noble metals, and other electronically conducting mixed oxides frequently composed of rare earth oxides mixed with oxides of cobalt, nickel, copper, iron, chromium and manganese, and combinations of such oxides. Preferred dopants are strontium, calcium, cobalt, nickel, iron, and tin.

Surrounding most of the outer periphery of the air electrode 28 is a layer of gas-tight solid electrolyte 30, generally comprised of yttria stabilized zirconia about 1 micron to about 100 microns thick, for the exemplary cell. The electrolyte 30 can be deposited onto the air electrode by well known high temperature vapor deposition techniques. However, a selected radial segment or portion 32 of the air electrode 28 is, for example, masked during electrolyte deposition, and a layer of a non-porous interconnect material 34 is deposited on this segment or portion 32.

The interconnect material 34, which preferably extends the active length of each elongated cell 12, must be electrically conductive in both an oxidant and fuel environment. Accordingly, the exemplary cell includes a gas-tight interconnection 34 roughly similar in thickness to the electrolyte, about 30 microns to about 100 microns.

The interconnect should be non-porous, have a resistivity of less than about 50 ohm-cm at 1000° C., and preferably be nearly 99% to 100% electronically conductive at 1000° C., the usual operating temperature of the fuel cell. It should also have other properties, such as, a moderate material cost, nearly invariant composition in both fuel and oxidant atmospheres, be non-reactive with other cell components at 1000° C., have negligible metal ion conduction, be free of destructive phase transformations in the region from 25° C. to 1200° C., have low volatility of oxide components in the working atmosphere, and be fabricable as a thin, oxygen gas or oxygen ion—impervious layer having minimal concentration of oxygen ion vacancies when exposed to a fuel atmosphere at 1200° C. Very importantly, the interconnect must have a coefficient of thermal expansion close to that of the solid electrolyte, and the electrode onto which it is deposited, and the other components, including the support tube which comprises the most volume in the fuel cell and is generally the thickest component of the fuel cell.

Undoped lanthanum chromite is not very useful as an electronic interconnection, due to its combination of marginal conductivity, mismatch of thermal expansion coefficient with the rest of the fuel cell components, and phase transition from orthorhombic to rhombohedral near 275° C. The use of lanthanum chromite doped solely with magnesium, such as $LaCr_{0.97}Mg_{0.03}O_3$, provides an interconnect material having good conductivity, but also having a substantially lower thermal expansion between 25° C. and 1000° C. than calcia stabilized zirconia support material, such as $(ZrO_2)_{0.85}(CaO)_{0.15}$ or solid electrolyte materials that are highly ion conductive at 1000° C., such as $(ZrO_2)_{0.9}(Y_2O_3)_{0.1}$.

Substitution of strontium, for part of the lanthanum in the interconnect material, in place of magnesium, to provide for example $La_{0.84}Sr_{0.16}CrO_3$, provides good conductivity, but leads to the formation of an appreciable concentration of oxygen ion vacancies when exposed to a fuel atmosphere at the high operating temperatures required for the high temperature fuel cell application. This, in turn, increases the rate of diffusion of oxygen through the interconnection, an undesirable trait which leads to some fuel loss by direct reaction with a small amount of oxygen leaking through the interconnection (instead of reacting at the electrolyte interfaces by the desired electrochemical process). Substitution of aluminum ion for an appreciable fraction of the chromium ion content of magnesium doped lanthanum chromite, to provide for example $LaCr_{0.72}Mg_{0.03}Al_{0.25}O_3$, leads to reduction in electrical conductivity due to the presence of the relatively large concentration of aluminum ions. In addition it has been found difficult to incorporate aluminum ion in the lanthanum chromite layer during fuel cell fabrication by the chemical vapor deposition process which has been used for thin layer, high temperature, solid electrolyte fuel cells.

It has been found that adding cobalt to the lanthanum chromite imparts good thermal expansion matching characteristics, approximating that of the solid electrolyte and electrode, and improves electronic conductivity at 1000° C., and such cobalt inclusion is critical to the high temperature properties of this invention. Additional inclusion of other selected elements provides even better electrical conductivity without substantially harming the other desired properties of the interconnect material mentioned before.

The general chemical formula representing the preferred interconnect materials of this invention is:

(I) $La_{1-z}M_zCr_{1-(x+y)}N_xCo_yO_3$, where M is an element selected from one or more of Sr, Ca, Y, Ce, and Yb; N is an element selected from either or both of Mg, and Al; Z=from 0 to about 0.1; x=from 0 to about 0.1; and y=from about 0.005 to about 0.1, preferably from about 0.02 to about 0.07. Thus, a material such as $LaCr_{1-y}Co_yO_3$ is possible, and very useful. The most preferred material is a lanthanum chromite double doped with magnesium and cobalt, which has the chemical formula:

(II) $LaCr_{1-(x+y)}Mg_xCo_yO_3$, where x=from about 0.005 to about 0.1, preferably from about 0.01 to about 0.05; and y=from about 0.005 to about 0.1, preferably from about 0.02 to about 0.07. An example of a preferred composition is $LaCr_{0.93}Mg_{0.03}Co_{0.04}O_3$.

The use of cobalt ion incorporation allows variability of interconnect thermal expansion to meet thermal expansion match-up characteristics, leads to minimal oxygen diffusion through the interconnection layer, and does not require any additional doping in order to obtain good electrical conductivity for fuel cell interconnect application. However, addition of magnesium in addition to cobalt gives an even better electrical conductivity though increasing somewhat its susceptibility to oxygen loss from the crystal lattice. The use of cobalt allows thermal expansion adjustment and improves conductivity.

These modified lanthanum chromite materials can be made by chemical vapor deposition techniques and a variety of known general techniques for making mixed oxide ceramics, including mixing, pressing and reactive sintering of the component metallic ion species present in the form of the individual oxides and other chemical forms which decompose to the oxides upon heating, such as the carbonates, oxalates, formates and hydroxides, and chemical mixtures formed by precipitation from solution. Methods involving organic resin formation followed by high temperature decomposition in an oxygen-containing atmosphere such as air are other useful methods.

Substantially surrounding the solid electrolyte 30 is a second porous electrode, for example, a nickel-zirconia or cobalt zirconia cermet fuel electrode, as anode 36. As shown, the anode 36 is also discontinuous, being spaced from the interconnection 34 a distance sufficient to avoid direct electrical communication between the anode 36 and both the interconnection 34 and the cathode 28. The exemplary anode 36 is about 100 microns thick.

Deposited over the interconnection 34 is an electrically conductive layer 38 which is preferably comprised of the same material as the fuel anode 36, nickel or cobalt zirconia cermet, and of about the same thickness, about 100 microns.

Figure 2:
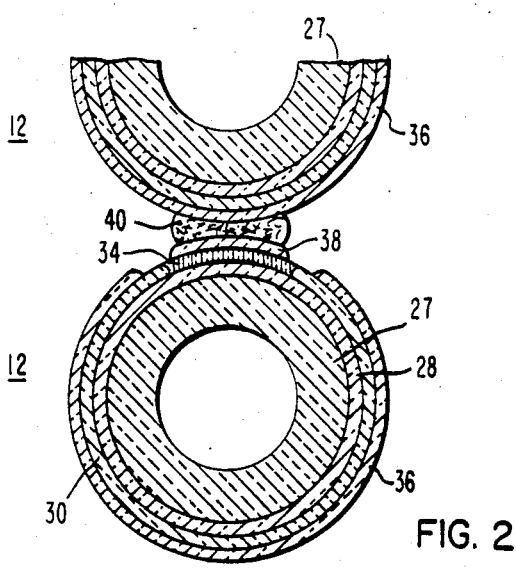
FIG. 2 is a section view through two adjacent fuel cells.

FIG. 2 shows the series electrical interconnection between consecutive fuel cells 12. The electrical interconnection is preferably enhanced by an optional metal felt 40, made, for example, of nickel fibers. The felt extends axially between the annular cells 12, and is bonded to each by pressure contact which causes sinter bonding during operation. In the inverted cell structure, where fuel flows inside of the cells, the felt material is made from conducting oxide fibers, such as doped $In_2O_3$ or others.

During operation, air, or $O_2$ flows through the center of the annular cells 12, and fuel passes over the exterior. Oxygen molecules diffuse through the porous support 27, and cathode 28. Fuel diffuses through the anode 36. Oxygen ions pass through the electrolyte 30. These reactants electrochemically interact via the actions of the electrolyte and electrodes in generating products such as water vapor and carbon dioxide, as well as heat and electrical energy. The high temperature water vapor and carbon dioxide are carried away from the cell with, for example, unburned fuel, and electrical power is transferred in series from the inner cathode 28 of one cell, through the electronic interconnect 34, conductive layer 38, and metal felt 40, to the outer anode electrode 36 of the second cell. The use of a highly conductive interconnect is essential to fuel cell generator operation. The electrical power is usefully drawn through leads not shown.

In the method of this invention, a porous calcia stabilized zirconia support tube, having, for example, a 1.5 millimeter wall thickness and a 13 millimeter outside diameter, is covered with 1 millimeter thickness of air electrode material, for example, doped lanthanum manganite. The air electrode layer is then masked over the radial segment where the interconnect is to be deposited later. The electrolyte is then applied by vapor deposition of metal oxides from gaseous $YCl_3$ and $ZrCl_4$, at about 1200° C. After demasking the radial segment, the interconnect material, for example, magnesium and cobalt doped lanthanum chromite, is applied over the doped lanthanum manganite air electrode layer by vapor deposition, using chloride vapors of chromium, lanthanum, magnesium, and cobalt. Finally the fuel electrode is applied over the electrolyte.

EXAMPLE 1

To investigate the bulk properties of various interconnect layer oxides, the component oxides were ground, mixed, pressed in a steel die at about 5,000 psi, and then sintered on platinum foil in an oven at about 1450° C., to form 1"×0.25"×0.25" bars having sample compositions 1 through 3 described further in Table 1. In a similar fashion, a bar of support tube material was also made. Four terminal resistance measurements were taken, and thermal expansion was measured using a dilatometer method. The results are shown below in Table 1, where Sample 1 is a comparative sample with no cobalt, Sample 6 is an unmodified lanthanum chromite with no magnesium or cobalt, Sample 4 is the support tube sample, and Sample 5 provides typical thermal expansion value for a solid oxide electrolyte material:

TABLE I

| Sintered Sample No. | Composition | Heat Treatment Temp, Time in Air | Average Thermal Expansion in M/M°C. over range 25° C. to 1000° C. |
|---|---|---|---|
| *1 | $LaCr_{.97}Mg_{.03}O_3$ | 1450° C.-2 hr. | ~8.9 × 10$^{-6}$ |
| 2 | $LaCr_{.94}Mg_{.03}Co_{.03}O_3$ | 1450° C.-2 hr. | ~9.8 × 10$^{-6}$ |
| 3 | $LaCr_{.92}Mg_{.03}Co_{.05}O_3$ | 1450° C.-2 hr. | ~10.3 × 10$^{-6}$ |
| **4 | $(ZrO_2)_{.85}(CaO)_{.15}$ | | ~10.0 × 10$^{-6}$ |
| **5 | $(ZrO_2)_{.9}(Y_2O_3)_{.1}$ | | ~10.0 × 10$^{-6}$ to ~10.5 × 10$^{-6}$ |
| *6 | $LaCrO_3$ | | ~9.0 × 10$^{-6}$ |

*Comparative Examples
**Standards: Sample 4 = support and Sample 5 = solid electrolyte As can be seen, Sample 1 (no cobalt) and Sample 6 (unmodified), have a substantially lower thermal expansion than Sample 4 (a typical support tube material for a high temperature fuel cell) or Sample 5 (a typical solid electrolyte composition). Sample 2, and Sample 3, having 3 and 5 atom percent cobalt substituted for the chromium of the basic $LaCrO_3$ composition respectively, provided much improved thermal matching to the component fuel cell materials of Samples 4 and 5, and also provided relatively low resistivity values, i.e., good electrical conductivity. Samples 2 and 3 also showed good temperature-time sintering parameters. With cobalt present, Sr, Ca, Y, Ce, Yb and Al can also be present in the composition with or without Mg, to still provide suitable conductivity values.

I claim:

1. In a high temperature, solid electrolyte electrochemical cell, subject to thermal cycling temperatures of between about 25° C. and about 1200° C., capable of electronic interconnection to at least one other electrochemical cell and capable of operating in an environment containing oxygen, said cell having two electrodes with solid electrolyte therebetween and an electronically conductive interconnect material disposed over a portion of one electrode, the improvement comprising an interconnect comprising a cobalt doped lanthanum chromite material, where the interconnect is characterized as being nearly impermeable to oxygen, and having a coefficient of thermal expansion that approximates the solid electrolyte in the temperature range of between about 25° C. and about 1200° C.

2. The electrochemical cell of claim 1, where the interconnect material is non-porous, and is about 99% to 100% electronically conductive at 1000° C.

3. The electrochemical cell of claim 1, where the interconnect is lanthanum chromite doped with both cobalt and magnesium.

4. The electrochemical cell of claim 1 electronically connected to at least one other electrochemical cell.

5. A high temperature, solid electrolyte electrochemical cell comprising:
(1) a first electrode,
(2) a solid electrolyte disposed on a portion of the first electrode,
(3) a second electrode disposed on a portion of the solid electrolyte,
(4) an electronically conductive interconnect material disposed on a portion of the first electrode and capable of allowing electronic interconnection to at least one other electrochemical cell, said interconnect material having the chemical formula:

$$La_{1-z}M_zCr_{1-(x+y)}N_xCo_yO_3,$$

where M is an element selected from the group consisting of Sr, Ca, Y, Ce, Yb, and mixtures thereof; N is an element selected from the group consisting of Mg, Al and mixtures thereof; $z=$ from 0 to about 0.1; $x=$ from 0 to about 0.1; and $y=$ from about 0.005 to about 0.1.

6. The electrochemical cell of claim 5, where, in the interconnect, N is Mg and $y=$ from about 0.02 to about 0.07.

7. The electrochemical cell of claim 5 being a fuel cell, where the interconnect material has the chemical formula:

$$LaCr_{1-(x+y)}Mg_xCo_yO_3,$$

where $x=$ from about 0.005 to about 0.1 and $y=$ from about 0.005 to about 0.1.

8. The fuel cell of claim 7, where, in the interconnect, $y=$ from about 0.02 to about 0.07.

9. The fuel cell of claim 7, electronically connected to at least one other fuel cell.

10. The fuel cell of claim 7, where the first electrode is applied to a support comprised of calcia stabilized zirconia, the first electrode is comprised of doped and undoped oxides or mixtures of oxides, the electrolyte is comprised of stabilized zirconia, and the second electrode is selected from the group consisting of nickel zirconia cermet and cobalt zirconia cermet.

11. A doped lanthanum chromite composition having the chemical formula:

$$La_{1-z}M_zCr_{1-(x+y)}N_xCo_yO_3,$$

where M is an element selected from the group consisting of Sr, Ca, Y, Ce, Yb, and mixtures thereof; N is an element selected from the group consisting of Mg, Al, and mixtures thereof; $z=$ from 0 to about 0.1; $x=$ from 0 to about 0.1; and $y=$ from about 0.005 to about 0.1.

12. A doped lanthanum chromite composition having the chemical formula:

$$LaCr_{1-(x+y)}Mg_xCo_yO_3,$$

where $x=$ from about 0.005 to about 0.1 and $y=$ from about 0.005 to about 0.1.

* * * * *